United States Patent [19]

Royer et al.

[11] 4,341,794
[45] Jul. 27, 1982

[54] 2-NITRONAPHTOFURAN DERIVATIVES AND USE AS CELL GROWTH REGULATORS

[75] Inventors: Rene R. Royer, Paris; Jean-Pierre Buisson, Sartrouville, both of France

[73] Assignee: Agence Nationale de Valorisation de la Recherche, Paris, France

[21] Appl. No.: 229,860

[22] Filed: Jan. 30, 1981

[30] Foreign Application Priority Data

Feb. 4, 1980 [FR] France .................................. 80 02354

[51] Int. Cl.$^3$ ................... A61K 31/345; C07D 307/92
[52] U.S. Cl. ..................................... 424/285; 549/458
[58] Field of Search ..................... 260/346.71; 424/285

[56] References Cited

U.S. PATENT DOCUMENTS 4,128,659 12/1978 Scherrer et al. .................... 424/285

FOREIGN PATENT DOCUMENTS 2424266 11/1979 France .

OTHER PUBLICATIONS

Weill-Thevenet et al., Mutation Research, vol. 88, (1981), pp. 355-362.

Primary Examiner—Richard Raymond
Attorney, Agent, or Firm—Armstrong, Nikaido, Marmelstein & Kubovcik

[57] ABSTRACT

Novel 2-nitronaphthofuran derivatives are of the formula

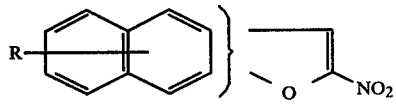

in which the linkage between the furan ring and the naphthalene nucleus is formed in the 1,2-, 2,3- or 2,1-positions of the naphthalene, and R, which can be located in a free position of the napthalene, represents a halogen atom or a methoxy group. They are prepared by condensing bromonitromethane with ortho-hydroxynaphthaldehydes and provide useful cell growth regulators.

5 Claims, No Drawings

2-NITRONAPHTOFURAN DERIVATIVES AND USE AS CELL GROWTH REGULATORS

FIELD OF THE INVENTION

This invention relates to 2-nitronaphthofuran derivatives and to their production and application as cell growth regulators.

BACKGROUND OF THE INVENTION

It is known that 2-nitrobenzofuran derivatives can be prepared by condensing bromonitromethane with salicylaldehydes (R. ROYER et al, Bull. Soc. Chim., 1970, 10, page 3,740).

SUMMARY OF THE INVENTION

We find that a range of novel compounds can be prepared by condensing bromonitromethane with or-thohydroxynaphthaldehydes and that, surprisingly, these compounds can be applied as cell growth regulators to achieve excellent results.

Such a compound is a 2-nitronaphthofuran derivative of the formula

I in which the linkage between the furan ring and the naphthalene nucleus is formed in a position selected from the 1,2-, 2,3- and 2,1-positions of the said naphthalene nucleus, and R, which can be located in any free position of the said napthalene nucleus, is selected from the group consisting of a halogen atom and a methoxy group.

The halogen atoms represented by R are, in particular, chlorine and bromine.

A compound of the invention can be prepared by condensing bromonitromethane with an ortho-hydroxynaphthaldehyde as mentioned above and in accordance with the following equation:

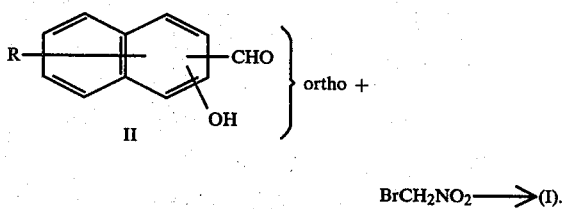

In the formula II, R has the same meaning as in the formula I.

This condensation is preferably carried out in the presence of an acid acceptor. In view of the fact that the ortho-hydroxyaldehydes II are suitable to a greater or lesser extent for a condensation of this type, it was appropriate to adapt the conditions thereof for each product. The condensation can therefore be carried out in the presence of potassium carbonate, either in water or in acetone, in the cold or under the action of heat, or alternatively in the presence of morpholine in accordance with a technique analogous to that described by L. RENE and R. ROYER (Eur. J. Med. Chem., 1979, 14, 471).

Some of the intermediate ortho-hydroxyaldehydes of the formula II are described in the literature, but the majority of them can hardly be obtained by the processes mentioned. The following methods are proposed:

1-formyl-2-hydroxy-3-methoxynaphthalene (II; $R=CH_3O$) can be prepared from 3-methoxynaphth-2-ol either by means of a Reimer-Tiemann reaction (compare ROYER et al., Bull. Soc. Chim., 1967, page 2,405) or by treatment with dichloromethyl methyl ether in the presence of $TiCl_4$;

the halogen derivatives, in particular 4-chloro-2-formyl-1-hydroxynaphthalene (II; R=Cl, described by W. J. BEGLEY and J. GRIMSHAW, J. Chem. Soc., Perkin Trans. I, 1975, page 1,840) and 6-bromo-1-formyl-2-hydroxynaphthalene (II; R=Br, described by E. MUNDLOS and T. PAPENFUHS, German Pat. No. 2,305,071 of Aug. 14, 1974), can be prepared respectively from 4-chloronaphth-1-ol and 6-bromonaphth-2-ol by treatment with dichloromethyl methyl ether; and 1-formyl-2-hydroxy-6-methoxynaphthalene (II; $R=CH_3O$, described by S. V. KESSAR et al., J. Indian Chem., 1973, page 624), 1-formyl-2-hydroxy-7-methoxynaphthalene (II; $R=CH_3O$, described by R. ADAMS et al., J. Amer. Chem. Soc., 1942 64, 1,795) and 2-formyl-3-hydroxy-5-methoxynaphthalene (II; $R=CH_3O$; new compound) can be prepared by the selective dimethylation, by means of aluminum chloride in methylene chloride, respectively of 2,6-dimethoxy-1-formylnaphthalene (N. P. BUU-HOÏ and D. LAVIT, J. Chem. Soc., 1955, page 2,776) 2,7-dimethoxy-1-formylnaphthalene (BUU-HOÏ, idem) and 3,5-dimethoxy-2-formylnaphthalene (R. A. BARNES and W. M. BUSCH, J. Amer. Chem. Soc., 1959, 81, 4,705).

DETAILED DESCRIPTION OF THE INVENTION

The following Examples illustrate the preparation of compounds of the invention and their cell growth regulating properties. Examples 1 and 2 relate to the preparation of the intermediates (II) and Example 3 relates to the preparation of the final compounds (I).

All the new compounds described here give percentage analyses for C, H and N which agree with theory to ±0.2%. They give $^1H$ NMR spectra which are compatible with their structures.

EXAMPLE 1

Formylation of 3-methoxynaphth-2-ol, 4-chloronaphth-1-ol and 6-bromonaphth-2-ol.

A solution made up of 2.1 moles of titanium tetrachloride and 1.1 moles of dichloromethyl methyl ether in 1 liter of freshly distilled methylene chloride is stirred for 15 minutes at 0° C. An amount proportional to 1 mole of the naphthol, dissolved in at least 1 liter of methylene chloride, is then added dropwise thereto, whilst keeping the temperature below 5° C. The mixture is left to stand at 5° C. for 2 hours, allowed to return to ambient temperature and poured into dilute hydrochloric acid, the resulting mixture is extracted with chloroform, the resins are filtered off if necessary, the extract is washed with water, the solvent is removed by heating under reduced pressure and the product is recrystallized. This yields respectively:

(a) 1-formyl-2-hydroxy-3-methoxynaphthalene, melting point=112° C. (from cyclohexane); yield: 65%;

(b) 4-chloro-2-formyl-1-hydroxynaphthalene, melting point=103° C. (from ethanol); yield: 79%; and (c) 6-bromo-1-formyl-2-hydroxynaphthalene, melting point=152° C. (from cyclohexane); yield 90%

EXAMPLE 2

Demethylation of dimethoxyformylnaphthalenes

These reactions were carried out with twice the amount by weight of aluminum chloride, in 1 liter of methylene chloride per mole of ether treated. The aluminum chloride is stirred in the methylene chloride at ambient temperature for 15 minutes and dimethoxyformylnaphthalene, dissolved in a minimum amount of methylene chloride, is then added slowly. The mixture is left to stand for 3 hours, whilst stirring, and poured into dilute hydrochloric acid, the resulting mixture is extracted with chloroform and the organic phase is washed with water and extracted with sodium hydroxide solution or potassium hydroxide solution. On neutralization with hydrochloric acid, the alkaline extract liberates:

(d) 1-formyl-2-hydroxy-6-methoxynaphthalene from 2,6-dimethoxy-1-formylnaphthalene, melting point=131°-132° C. (from toluene); yield: 80%;

(e) 1-formyl-2-hydroxy-7-methoxynaphthalene from 2,7-dimethoxy-1-formylnaphthalene, melting point=128°-129° C. (from toluene); yield: 87%; and (f) 2-formyl-3-hydroxy-5-methoxynaphthalene from 3,5-dimethoxy-2-formylnaphthalene, melting point=107° C. (from cyclohexane); yield: 85%.

EXAMPLE 3

Condensation of the ortho-hydroxyaldehydes (II) with bromonitromethane.

TECHNIQUE A (in acetone at 0° C.)

A solution formed of an amount of bromonitromethane corresponding to 2 moles, in 500 ml of acetone, is added dropwise, whilst stirring vigorously and keeping the temperature at 0° C., to a mixture made up of amounts proportional to 1 mole of the appropriate aldehyde (II) and of 2 moles of potassium carbonate in 3 liters of pure acetone. Stirring is continued at 0° C. for 2 hours and the mixture is allowed to return gradually to ambient temperature, left to stand for 18 hours and then heated at the boil, under reflux, for 2 hours. It is filtered, the inorganic residue is washed with acetone and the solvent is evaporated off from the organic phase. The resulting product is taken up in chloroform and chromatographed on an alumina column, elution being carried out with the same solvent. Finally, the product is recrystallized from benzene or alcohol or a mixture of these two solvents.

TECHNIQUE B (in boiling acetone)

The same mixture as above of aldehyde (II) and potassium carbonate in acetone is heated to the boil before the bromonitromethane, dissolved in acetone, is added dropwise thereto. After the addition has ended, heating at the boil is continued for 4 hours, the following treatment being the same.

TECHNIQUE C (in water at 20° C.)

Amounts proportional to 1 mole of hydroxyaldehyde (II) and 2 moles of potassium carbonate in 35 liters of water are kept at ambient temperature for 1 hour, whilst stirring. The amount corresponding to 1.5 moles of bromonitromethane, in 300 ml of ethanol, is added slowly and the mixture is left to stand for 48 hours, whilst stirring. The precipitate is filtered off, washed with water and dissolved in chloroform. The treatment is completed as in the above techniques.

TECHNIQUE D (in boiling water)

The same aqueous solution as above of orthohydroxyaldehyde (II) and potassium carbonate is heated at the boil for 1 hour, under reflux. 1.5 moles of bromonitromethane are then added rapidly thereto and heating is continued for 1 hour, whilst stirring. The mixture is left to cool and treated according to use.

TECHNIQUE E (with morpholine)

A 10% strength benzene solution of a mixture of 1 mole of ortho-hydroxyaldehyde (II) and 2 moles of morpholine is heated at the boil, under reflux, in an apparatus fitted with a water collector. When the desired amount of water has separated out, the mixture is cooled externally in ice, 1.1 moles of bromonitromethane are added all at once and the resulting mixture is then left to stand for 15 hours at ambient temperature and finally heated at the boil for 1 hour. It is washed carefully with water and filtered on an alumina column and elution is completed with chloroform.

The yields of these various preparations, obtained for each product synthesized, are indicated in the following table by way of comparison.

| o-Hydroxy-aldehydes (II) | No. | Melting point °C. | 2-Nitronaphthofurans (I) Yield (%), according to the technique of preparation | | | | |
|---|---|---|---|---|---|---|---|
| | | | A | B | C | D | E |
| a | 1 | 180 | 25 | 21 | 44 | 34 | 50 |
| c | 2 | 250 | 21 | 17 | 43 | 47 | 27.5 |
| d | 3 | 188 | 66 | 30 | 8 | 55 | 10 |
| e | 4 | 200 | 65 | 28 | 13 | 42 | 75 |
| b | 5 | 165 | 25 | 16 | 16 | 8 | 72 |
| f | 6 | 199 | 4 | 4 | 0 | 0 | 62 |

The structural formulae and the nomenclatures of the various compounds above are as follows:

Compound No. 1

2-nitro-4-methoxynaphtho[2,1-b]furan

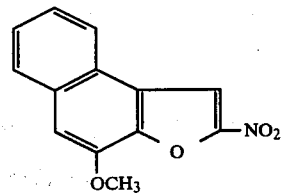

Compound No. 2

2-nitro-7-bromonaphtho[2,1-b]furan

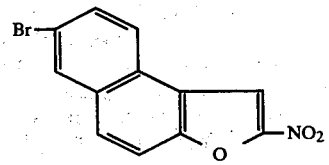

Compound No. 3

2-nitro-7-methoxynaphtho[2,1-b]furan

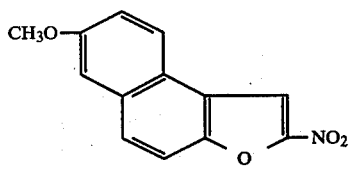

Compound No. 4

2-nitro-8-methoxynaphtho[2,1-b]furan

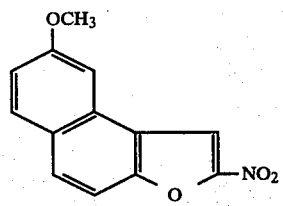

Compound No. 5

2-nitro-5-chloronaphtho[1,2-b]furan

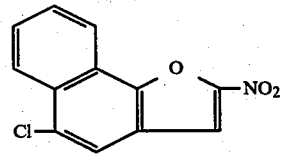

Compound No. 6

2-nitro-8-methoxynaphtho[2,3-b]furan

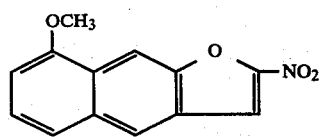

The compounds of the invention were subjected to a biological experiment on microorganisms.

Mutagenicity of the compounds was detected by means of a qualitative test on strains of Salmonella TA 1537, TA 1538 and TA 98 from the Institut Pasteur collection. These experiments were carried out with or without activation and the measurement of the mutagenicity showed that it is sensitive to the presence of the activation mixture, which has a detoxifying action.

It was found, in particular, that Compound No. 3 of the invention (the presently preferred embodiment) possesses a mutagenicity 1,000 times higher than that of the reference mutagen ICR 191.

In view of their high mutagenicity, compounds of the invention can be used as laboratory reagents, in particular as cell growth regulators, for example as reference mutagens.

We claim:

1. A 2-nitronaphthofuran derivative of the formula

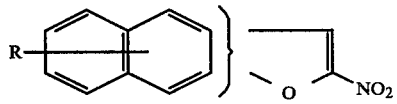

I in which the linkage between the furan ring and the naphthalene nucleus is formed in a position selected from the 1,2-, 2,3- and 2,1- positions of the said naphthalene nucleus, and R, which can be located in any free position of the said naphthalene nucleus, is selected from the group consisting of a halogen atom and a methoxy group.

2. A 2-nitronaphthofuran derivative according to claim 1, in which R is a methoxy group.

3. A 2-nitronaphthofuran derivative according to claim 1, in which R is a chlorine or bromine atom.

4. 2-Nitro-7-methoxynaphtho[2,1-b]furan.

5. A method of regulating cell growth which comprises administering to the cells a cell growth regulating amount of a 2-nitronaphthofuran derivative of the formula

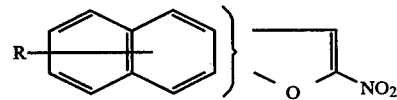

I in which the linkage between the furan ring and the naphthalene nucleus is formed in a position selected from the 1,2-, 2,3- and 2,1- positions of the said naphthalene nucleus, and R, which can be located in any free position of the said naphthalene nucleus, is selected from the group consisting of a halogen atom and a methoxy group.

* * * * *